(12) United States Patent
Shows

(10) Patent No.: US 7,017,283 B2
(45) Date of Patent: Mar. 28, 2006

(54) FOOT PAIN-RELIEVING ARTICLES AND METHODS THEREOF

(76) Inventor: Michael David Shows, 7176 Ranchito Cir., Las Vegas, NV (US) 89120

( * ) Notice: Subject to any disclaimer, the term of this patent is extended or adjusted under 35 U.S.C. 154(b) by 274 days.

(21) Appl. No.: 10/637,232

(22) Filed: Aug. 11, 2003

(65) Prior Publication Data

US 2005/0034335 A1 Feb. 17, 2005

(51) Int. Cl.
*A43B 7/06* (2006.01)

(52) U.S. Cl. ........................................................ 36/3 B
(58) Field of Classification Search ................ 36/3 B, 36/3 A, 3 R, 26
See application file for complete search history.

(56) References Cited

U.S. PATENT DOCUMENTS 5,375,430 A * 12/1994 Siegel ........................ 62/259.3
6,510,624 B1 * 1/2003 Lakic ............................ 36/29
6,725,573 B1 * 4/2004 Doyle ............................ 36/29
6,865,825 B1 * 3/2005 Bailey et al. ............... 36/88

* cited by examiner

*Primary Examiner*—Ted Kavanaugh
(74) *Attorney, Agent, or Firm*—Harry M. Weiss; Weiss, Moy & Harris, P.C.

(57) ABSTRACT

Articles that provide foot pain-relief for wearers of shoes and methods are disclosed. The foot pain-relief articles comprise removable inserts for foot wear that are activated by exposure to air or breaking an internal bag of the insert and shaking the inserts to provide single use disposable inserts. The disposable inserts provide warming or cooling for an extended period of time for foot pain-relief. A reusable insert is disclosed that is activated by refrigeration or by heating to provide either cooling or warming foot pain-relief. Foot pain relief by cooling of foot wear is provided by foot wear comprising a chamber and an aperture for a compressed gas cylinder. The chamber is recharged as needed to provide continuous cooling of a foot.

9 Claims, 2 Drawing Sheets

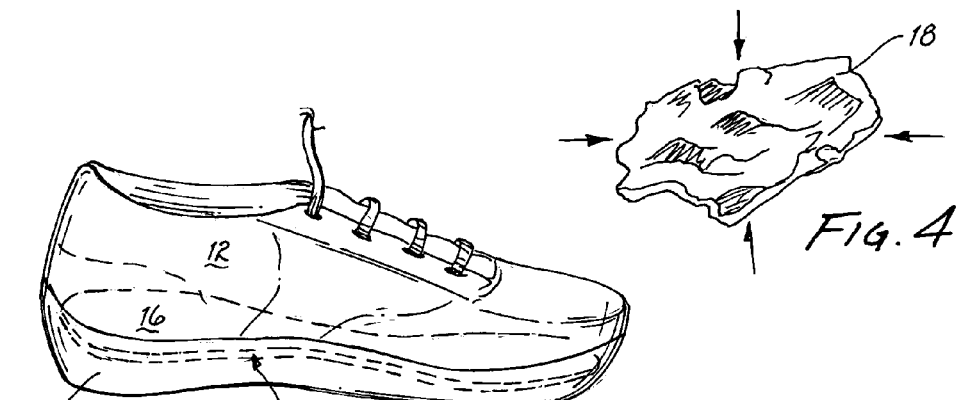
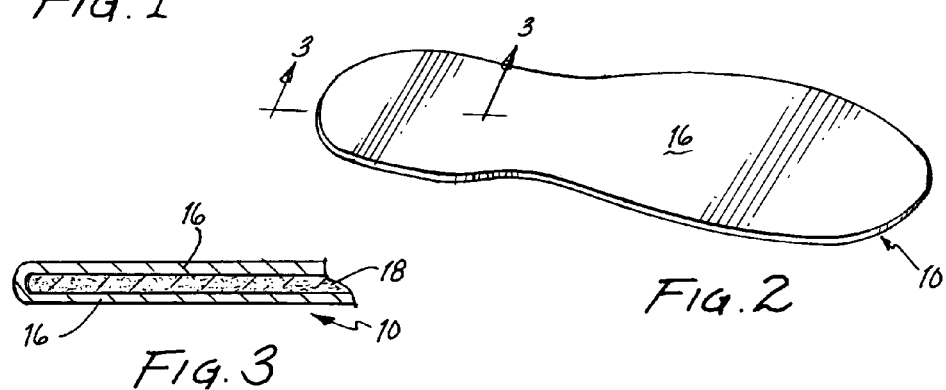
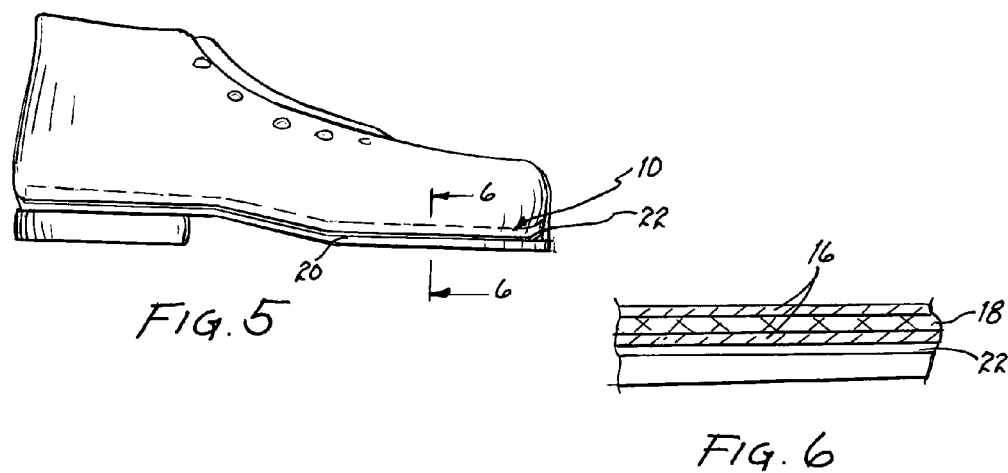

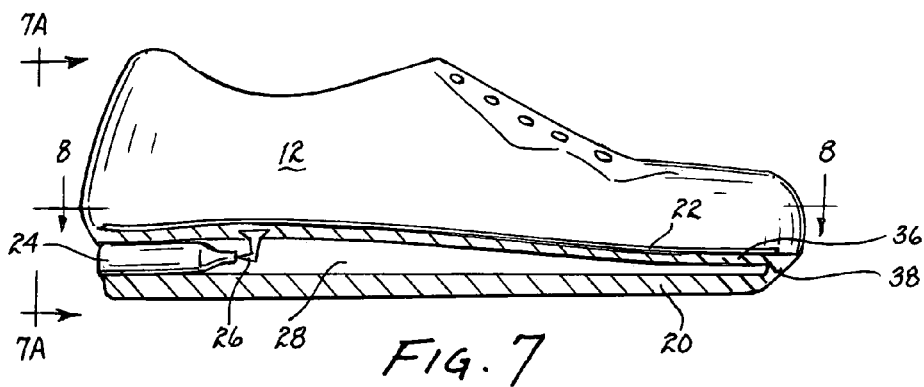
FIG. 7
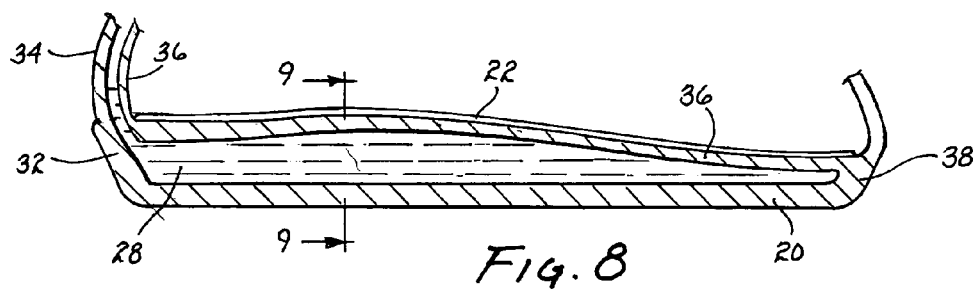
FIG. 8
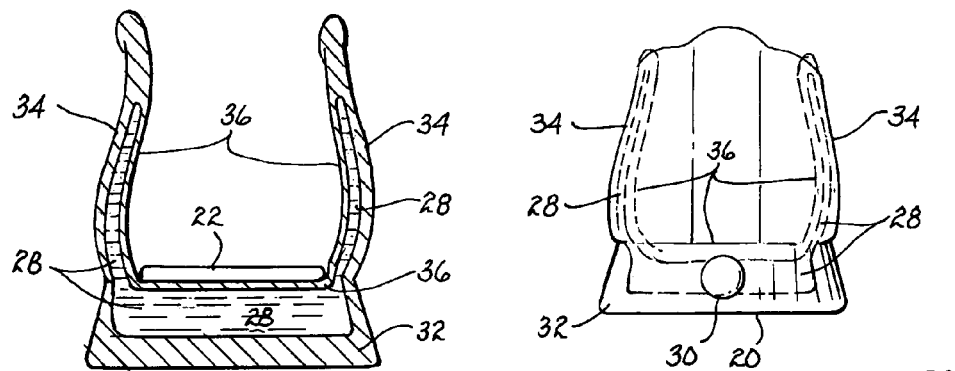
FIG. 9
FIG. 7A

FOOT PAIN-RELIEVING ARTICLES AND METHODS THEREOF

FIELD OF THE INVENTION

This invention relates generally to foot pain-relief and more particularly to articles that provide foot pain-relief articles for foot wear and methods thereof.

BACKGROUND OF THE INVENTION

In the past, numerous articles were used for providing foot pain-relief. Typically, such articles were incorporated into the shape of footwear, such as a specific kind of molding to support arches of a foot in a shoe. Other articles were provided as inner sole inserts that were also specifically molded to provide foot support for a wearer of a shoe.

More recently, foot support has been achieved by the use of a liquid filled bladder (see French, U.S. Pat. No. 5,806,208). The liquid provides massaging action by way of special rib designs and valves, which direct flow of the liquid. In addition, in French, U.S. Pat. No. 5,806,208 replaceable liquids can be placed in the bladder to provide for cooling and warming of a specific shoe that is fitted with the bladder. French's shoe with a bladder U.S. Pat. No. 5,806,208 generally comprises an integral sole portion of the shoe that fits as an integral insole of the shoe and integral fingers extending from the integral sole portion. Also, the cooling and warming liquids are preferably introduced by means of a supply port so that the user can change or add liquid to the bladder. Re-introduction of the cooling or warming liquid is necessary for achieving cooling or warming in the shoe. Alternatively, placing the entire shoe structure into a cooler for cooling in the shoe or a microwave oven (or other heating source) for warming in the shoe achieves the same result.

It is desirable to provide means for cooling or warming shoes that do not depend on refilling a shoe with a liquid as provided for in French, U.S. Pat. No. 5,806,208) or that do not depend on placing the entire shoe into a cooler for cooling the shoe or into a heat source such as a microwave oven for warming of the shoe. Current devices and methods for achieving such means are not available.

For the foregoing reasons, there is a need to provide improved articles that provide foot pain-relief for wearers of shoe and methods thereof. This invention provides foot pain-relief articles that use liquids, solids or gases to warm or cool the feet of wearers of shoes.

SUMMARY OF THE INVENTION

Accordingly, it is an object of this invention to provide improved articles that provide foot pain-relief for wearers of shoes.

It is a further object of this invention to provide improved articles that provide foot pain-relief for shoe wearers, which use liquids, solids or gases to warm or cool the feet of wearers of shoes.

It is yet a still further object of this invention to provide improved articles that provide foot pain-relief for wearers of shoes that may be integral or removable from shoes.

It is a further object of this invention to provide methods for providing foot-pain relief for wearers of shoes.

PREFERRED EMBODIMENTS OF THE INVENTION

In accordance with one embodiment of this invention, a foot pain-relief article for foot wear is disclosed. The foot pain-relief article comprises a foot wear product; an insert adapted to be used with the foot wear product; and means incorporated as at least a portion of the insert for providing foot pain-relief for an extended period of time for a foot of a user of the foot wear product when the foot pain-relief means of the insert is activated. The foot pain-relief means comprises the insert having an outer layer for enclosing a reactive core. The insert coupled to an insole of the foot wear is removable. In one example, the reactive core provides warming of the insert when the insert is exposed to air. In a second example, the reactive core comprises an internal bag that provides cooling of the insert when the internal bag of the insert is broken and the insert is shaken. In a third example, the reactive core comprises a fluid having a high heat capacity to provide warming of the insert when the insert is heated by an exterior heating source and the reactive core provides cooling of the insert when the insert is cooled by an exterior cooling source.

In accordance with a second embodiment, a cooling foot pain-relief article for foot wear is disclosed. The cooling foot pain-relief article comprises a foot wear product; a chamber incorporated within the foot wear product and means adapted to be activated by a person for internally cooling the chamber of the foot wear product to thereby cool the foot wear product and a foot of a user of the foot wear product. The means adapted to be activated by a person for internally cooling the chamber of the foot wear product comprises a compressed gas cylinder coupled to the foot wear product. The chamber is defined by a portion of a foot wear product upper, a portion of a heel, a portion of a sole, a portion of a toe and a portion of a foot wear product inner for enclosing a cooling gas in the chamber. The foot wear product has an aperture for receiving the compressed gas cylinder to provide the cooling gas to the chamber. A valve system retains the cooling gas in the chamber when the compressed gas cylinder is withdrawn from the aperture and displaces the spent cooling gas when the chamber is recharged with another compressed gas cylinder for re-cooling the chamber. A spike is coupled to a portion of the chamber for piercing the compressed gas cylinder to release the cooling gas into the chamber. The cooling gas is non-flammable. The cooling gas is carbon dioxide.

In accordance with a third embodiment, a method for providing cooling foot pain-relief for foot wear is disclosed. The method comprises the steps of providing a foot wear product having a chamber incorporated within the foot wear product; and providing means for cooling the chamber of the foot wear product to thereby cool the foot wear product and a foot of a user of the foot wear product. The means for cooling the foot wear product comprises a compressed gas cylinder coupled to the foot wear product and the chamber is defined by a portion of a foot wear product upper, a portion of a heel, a portion of a sole, a portion of a toe and a portion of a foot wear product inner for enclosing a cooling gas in the chamber. The method provides that the foot wear product has an aperture for receiving the compressed gas cylinder to provide the cooling gas to the chamber; provides a valve system for retaining the cooling gas in the chamber when the compressed gas cylinder is withdrawn from the aperture; recharges the chamber with another compressed gas cylinder for re-cooling the chamber; and displaces the spent cooling gas using the valve system when the chamber is recharged. The method provides a spike coupled to a portion of the chamber; and the spike pierces the compressed gas cylinder to release the cooling gas into the chamber.

In a fourth embodiment, a method for providing foot pain-relief for foot wear is disclosed. The method comprises providing a foot wear product; providing an insert adapted to be used with the foot wear product; and providing means incorporated as at least a portion of the insert for providing foot pain-relief for an extended period of time for a foot of a user of the foot wear product when the foot pain-relief means of the insert is activated. The method provides the foot pain-relief means comprises the insert having an outer layer for enclosing a reactive core; activating the insert to provide cooling or warming of the foot wear product; and coupling the insert to an insole of the foot wear product so that the insert is removable when the insert is no longer active.

The foregoing and other objects, features, and advantages of the invention will be apparent from the following, more detailed description of the preferred embodiments of the invention, as illustrated in the accompanying drawings.

BRIEF DESCRIPTION OF THE DRAWINGS

FIG. 1 is a perspective view of a shoe with a removable insert on an insole of the shoe, that either warms or cools a foot according to the invention;

FIG. 2 is a perspective view of the removable insert of FIG. 1;

FIG. 3 is an enlarged sectional view through 3—3 of the removable insert of FIG. 2;

FIG. 4 is an enlarged perspective view of a portion of a semi-solid core of the removable insert used in FIG. 1;

FIG. 5 is an elevation view of a boot with a removable insert on an insole of the boot, that either warms or cools a foot according to the invention;

FIG. 6 is a sectional view through 6—6 of the removable insert, the insole and the sole of the boot of FIG. 5;

FIG. 7 is an elevation view of a shoe with a cut-away view of a bottom portion of the shoe showing a compressed gas cylinder proximate to a spike in a chamber of the bottom portion of the shoe and with the gas cylinder inserted into a heel of the shoe;

FIG. 7A is an elevation view of a rear portion of the shoe with an opening for receiving the compressed cylinder in the heel of the shoe of FIG. 7;

FIG. 8 is a partial sectional view along 8—8 of the shoe of FIG. 7 showing a portion of a shoe upper, a heel, a sole, a portion of a toe, a portion of a shoe inner proximate to an insole and an upper portion of a shoe inner enclosing the chamber filled with a gas; and FIG. 9 is a sectional view through 9—9 of the shoe of FIG. 7 providing further detail of a portion of the shoe upper, the heel, the sole, the portion of the shoe inner proximate to the insole and an upper portion of the shoe inner enclosing the chamber filled with the gas.

DESCRIPTION OF THE INVENTION

According to FIG. 1, an insert 10 is coupled to a portion of a surface of an insole 22 of a shoe 12. According to FIGS. 2 and 3 the insert 10 comprises an outer layer 16 and a core 18 enclosed by the outer layer 16. FIG. 3 shows the core 18 enclosed within the outer layer 16 in better detail. The core 18 comprises a reactive material.

FIG. 4 shows an enlarged perspective view of a semi-solid core of the removable insert 10. The core 18 is activated by exposing the insert 10 to air or by breaking an inner bag (not shown) of the insert 10 and shaking the insert 10. In a first example, the core 18 comprises a combination of iron powder, water, activated carbon, vermiculite, salt, wooden powder and PURGE™ natural mineral powder, obtainable as a product named BEYOND BODI HEAT® (made by Okamoto Industries Inc., Japan). When the insert 10, comprising BEYOND BODI HEAT® is exposed to air, the insert 10 heats up exothermically to maintain an average temperature of 104° F. for 12 hours. The insert 10, comprising BEYOND BODI HEAT® as the core 18 is disposed after use, but requires no outside source other than exposure to air to activate the product.

In a second example, the core 18 comprises an inner bag (not shown) separating ammonium nitrate and water. On breaking the inner bag and shaking the insert 10 the ammonium nitrate dissolves in water resulting in endothermic dissolution with resulting cooling of the mixture of ammonium nitrate and water. THERA-MED® (Thera-Med, Inc., Waco Tex., U.S.A.) is an example of a commercially available ammonium nitrate based product. The insert 10, comprising THERA-MED® as the core 18 is disposed after use, but requires no outside source other than breaking the inner bag and shaking the insert 10 to activate the insert 10.

In a third example, the core 18 comprises a gel pack. The insert 10 comprising the gel pack core 18 may either be placed into a refrigerator for cooling or into a microwave oven for heating. TRU-FIT™ I.C.E./HEAT (distributed by BD™ Consumer Healthcare, Franklin Lakes, N.J., U.S.A.) is an example of a commercially available Gel Pack consisting essentially of a high heat capacity solution of a polyacrylamide in water. The insert 10, comprising TRU-FIT™ I.C.E./HEAT as the core 18 is reusable but requires an outside source to activate the product.

FIG. 5 is an elevation view of a boot 14 with a removable insert 10 coupled to an insole 22 of the boot 14 that either warms or cools a foot as described above for a shoe 12. A warming disposable insert 10 for the boot 14 is of particular value to a mountain climber or to a hiker in a cold climate. A cooling disposable insert 10 for the boot 14 is of particular value to a hiker or to a soldier in a hot climate. FIG. 6 is a sectional view through 6—6 of the removable insert 10, the insole 22 and a sole 20 of the boot 14. The removable insert 10 is either placed on the insole 22 or coupled to the insole 22 by means of a pressure sensitive adhesive.

Referring to FIG. 7 a shoe 12 comprises a chamber 28 of a portion of a shoe 12 for enclosing a gas that is released when a compressed gas cylinder 24 is pierced by a spike 26 in the chamber 28 of the shoe 12. The spike 26 is coupled to a portion of a surface of a shoe inner 36. The release of gas from the compressed gas cylinder 24 results in cooling of the shoe inner 36. In FIG. 7A a heel 32 of the shoe 12 defines an aperture 30 for receiving the compressed gas cylinder 24. A valve system (not shown) prevents gas escaping from the chamber 28 when the compressed gas cylinder 24 is pierced by the spike 26 and also after the empty compressed gas cylinder 24 is withdrawn. Another valve system (not shown) may be provided for exhausting the gas before refilling the chamber 28 with the gas. The shoe 12 may be recharged with the gas as needed to continue cooling the shoe 12. FIG. 7A is also shows that the chamber 28 is contiguous with a portion of a shoe upper 34 (see dashed lines). Any gas that is non-flammable and non-toxic may be used, but carbon dioxide is a preferred as in the compressed gas cylinder 24.

FIG. 8 is a partial sectional view along 8—8 of the shoe 12 showing a portion of the shoe upper 34, the heel 32 and a sole 20, a portion of a toe 38, a portion of the shoe inner 36 proximate to the insole 22 and an upper portion of the shoe inner 36 enclosing the chamber 28 filled with the gas.

It is understood that a portion of the chamber 28 proximate to the toe 38 may extend to an upper portion of the shoe 12. FIG. 9 is a sectional view through 9—9 of the shoe 12 providing further detail of a portion of the shoe upper 34, the heel 32, the sole 20, the portion of the shoe inner 36 proximate to the insole 22 and an upper portion of the shoe inner 36 enclosing the chamber 28 filled with the gas. According to both FIGS. 8 and 9 when the chamber 28 is filled with the gas, cooling is provided throughout the shoe 12.

In summary, articles that provide foot pain-relief for wearers of shoes and methods are disclosed. The foot pain-relief articles comprise removable inserts for foot wear that are activated by exposure to air or breaking an internal bag of the insert and shaking the inserts to provide single use disposable inserts. The disposable inserts provide warming or cooling for an extended period of time for foot pain-relief. A reusable insert is disclosed that is activated by refrigeration or by heating to provide either cooling or warming foot pain-relief. Foot pain relief by cooling of foot wear is provided by foot wear comprising a chamber and an aperture for a compressed gas cylinder. The chamber is recharged as needed to provide continuous cooling of a foot.

While the invention has been particularly shown and described with reference to preferred embodiments thereof, it will be understood by those skilled in the art that the foregoing and other changes in form and details may be made therein without departing from the spirit and scope of the invention. For example, the outer layer of the insert may comprise various layers of materials including various core layers for providing cooling or warming of foot wear. Different kinds of materials may be used as the core constituents, which provide warming or cooling effects. A compressed gas cylinder comprising a valve and an inlet spout may be used to provide cooling gas into cooling chambers of foot wear. The compressed gas cylinder may be introduced into the chamber of the shoe from an aperture in the sole of the shoe. The chamber of the shoe may include a fluid for providing more efficient cooling when cooling gas is introduced into the chamber.

What is claimed is:

1. A cooling foot pain-relief article for footwear comprising, in combination: a footwear product; a single continuous interior chamber incorporated within an enclosed bottom portion of the footwear product and extending across substantially an entire width and an entire length of said enclosed bottom portion of said footwear product; and
    a source of a gas fluid adapted to be introduced through an aperture in a rear portion of said footwear product into said chamber and adapted to be activated by a person for internally cooling said chamber of the footwear product to thereby cool the footwear product and a foot of a user of the footwear product.

2. The cooling foot pain-relief article for footwear according to claim 1 wherein said source of a gas fluid comprising a compressed gas cylinder coupled to the footwear product.

3. The cooling foot pain-relief article for footwear according to claim 1 wherein said chamber defined by a portion of a footwear product upper, a portion of a heel, a portion of a sole, a portion of a toe and a portion of a footwear product inner for enclosing a cooling gas in said chamber.

4. A cooling foot pain-relief article for footwear comprising, in combination: a footwear product; a chamber incorporated within the footwear product and a source of a gas fluid adapted to be activated by a person for internally cooling said chamber of the footwear product to thereby cool the footwear product and a foot of a user of the footwear product; wherein said chamber defined by a portion of a footwear product upper, a portion of a heel, a portion of a sole, a portion of a toe and a portion of a footwear product inner for enclosing a cooling gas in said chamber; further comprising a spike coupled to a portion of said chamber for piercing a compressed gas cylinder containing a cooling gas to release the cooling gas into said chamber.

5. The cooling foot pain-relief article for footwear according to claim 3 wherein the cooling gas is non-flammable.

6. The cooling foot pain-relief article for footwear according to claim 3 wherein the cooling gas is carbon dioxide.

7. A method for providing cooling foot pain-relief for footwear comprising the steps of: providing a footwear product having a single continuous interior chamber incorporated within an enclosed bottom portion of the footwear product and extending across substantially an entire width and an entire length of said enclosed bottom portion of said footwear product; and providing a source of a gas fluid adapted to be introduced through an aperture in a rear portion of said footwear product into said chamber and adapted to be activated by a person for internally cooling said chamber of the footwear product to thereby cool the footwear product and a foot of a user of the footwear product.

8. The method for providing cooling foot pain-relief for footwear according to claim 7 further comprising the steps of: providing said source of a gas fluid as a compressed gas cylinder coupled to the footwear product; and providing said chamber defined by a portion of a footwear product upper, a portion of a heel, a portion of a sole, a portion of a toe and a portion of a footwear product inner for enclosing a cooling gas in said chamber.

9. A method for providing cooling foot pain-relief for footwear comprising the steps of: providing a footwear product having a chamber incorporated within the footwear product; and providing a source of a gas fluid for cooling said chamber of the footwear product to thereby cool the footwear product and a foot of a user of the footwear product; further comprising the steps of: providing said source of a gas fluid as a compressed gas cylinder coupled to the footwear product; and providing said chamber defined by a footwear product upper and further comprising the steps of: providing a spike coupled to a portion of said chamber; and said spike piercing said compressed gas cylinder to release a cooling gas contained therein into said chamber.

* * * * *